(12) United States Patent
Suchanek et al.

(10) Patent No.: US 10,124,318 B2
(45) Date of Patent: Nov. 13, 2018

(54) METHOD FOR PRODUCING POROUS BODIES WITH ENHANCED PROPERTIES

(71) Applicant: Scientific Design Company, Inc., Little Ferry, NJ (US)

(72) Inventors: Wojciech L. Suchanek, Wyckoff, NJ (US); Matthew Julian, Yorktown, VA (US)

(73) Assignee: Scientific Design Company, Inc., Little Ferry, NJ (US)

( * ) Notice: Subject to any disclaimer, the term of this patent is extended or adjusted under 35 U.S.C. 154(b) by 268 days.

(21) Appl. No.: 15/171,273

(22) Filed: Jun. 2, 2016

(65) Prior Publication Data

US 2016/0354759 A1 Dec. 8, 2016

Related U.S. Application Data

(60) Provisional application No. 62/169,766, filed on Jun. 2, 2015, provisional application No. 62/169,706, filed on Jun. 2, 2015.

(51) Int. Cl.
| | | |
|---|---|---|
| B01J 21/04 | (2006.01) | |
| B01J 35/04 | (2006.01) | |
| C04B 35/06 | (2006.01) | |
| B01J 35/10 | (2006.01) | |
| C07D 301/22 | (2006.01) | |
| B01J 37/00 | (2006.01) | |
| B01J 37/08 | (2006.01) | |
| B01J 23/50 | (2006.01) | |
| C04B 38/00 | (2006.01) | |
| C07D 301/10 | (2006.01) | |
| C04B 41/88 | (2006.01) | |
| C04B 38/08 | (2006.01) | |
| C04B 41/00 | (2006.01) | |
| C04B 41/51 | (2006.01) | |
| B01J 19/00 | (2006.01) | |
| B01J 23/04 | (2006.01) | |
| B01J 23/36 | (2006.01) | |
| C04B 41/45 | (2006.01) | |
| C04B 111/00 | (2006.01) | |

(52) U.S. Cl.
CPC ............ *B01J 21/04* (2013.01); *B01J 19/0013* (2013.01); *B01J 23/04* (2013.01); *B01J 23/36* (2013.01); *B01J 23/50* (2013.01); *B01J 35/04* (2013.01); *B01J 35/108* (2013.01); *B01J 35/1009* (2013.01); *B01J 35/1038* (2013.01); *B01J 35/1042* (2013.01); *B01J 35/1047* (2013.01); *B01J 37/0018* (2013.01); *B01J 37/086* (2013.01); *C04B 38/00* (2013.01); *C04B 38/08* (2013.01); *C04B 41/009* (2013.01); *C04B 41/4535* (2013.01); *C04B 41/5116* (2013.01); *C04B 41/88* (2013.01); *C07D 301/10* (2013.01); *C07D 301/22* (2013.01); *B01J 2219/00051* (2013.01); *C04B 2111/0081* (2013.01)

(58) Field of Classification Search
CPC ............ B01J 21/04; B01J 35/04; C04B 38/06
See application file for complete search history.

(56) References Cited

U.S. PATENT DOCUMENTS

| | | | |
|---|---|---|---|
| 3,563,914 A | 2/1971 | Wattimena | |
| 3,702,259 A | 11/1972 | Nielsen | |
| 4,761,394 A | 8/1988 | Lauritzen | |
| 4,766,105 A | 8/1988 | Lauritzen | |
| 4,908,343 A | 3/1990 | Bhasin | |
| 5,011,807 A | 4/1991 | Hayden et al. | |
| 5,057,481 A | 10/1991 | Bhasin | |
| 5,099,041 A | 3/1992 | Hayden et al. | |
| 5,102,848 A | 4/1992 | Soo et al. | |
| 5,187,140 A | 2/1993 | Thorsteinson et al. | |
| 5,407,888 A | 4/1995 | Herzog et al. | |
| 5,801,259 A | 9/1998 | Kowaleski | |
| 8,895,469 B2 * | 11/2014 | Chen | B01J 21/04 502/100 |
| 8,937,031 B2 | 1/2015 | Lockemeyer et al. | |
| 9,776,169 B2 * | 10/2017 | Suchanek | B01J 23/50 |
| 2005/0096219 A1 | 5/2005 | Szymanski et al. | |
| 2008/0138569 A1 | 6/2008 | Collier et al. | |
| 2009/0227820 A1 | 9/2009 | Pak et al. | |
| 2012/0108832 A1 * | 5/2012 | Chen | B01J 21/04 549/536 |
| 2012/0323026 A1 | 12/2012 | Lockemeyer et al. | |
| 2014/0100379 A1 | 4/2014 | Richard et al. | |
| 2018/0021755 A1 * | 1/2018 | Suchanek | B01J 23/50 502/348 |

FOREIGN PATENT DOCUMENTS

| | | |
|---|---|---|
| EP | 0327356 A1 | 8/1989 |
| WO | 9623585 A1 | 8/1996 |
| WO | 2014189741 A2 | 11/2014 |

OTHER PUBLICATIONS

Ghanbarian, B., et al., "Tortuosity in Porous Media: A Critical Review", Soil Sci. Soc. Am. J., Sep. 20, 2013, pp. 1461-1477, 77.

(Continued)

Primary Examiner — Karl E Group
(74) Attorney, Agent, or Firm — Scully Scott Murphy and Presser

(57) ABSTRACT

A precursor mixture for producing a porous body, wherein the precursor mixture comprises: (i) milled alpha alumina powder having a particle size of 0.1 to 6 microns, (ii) boehmite powder that functions as a binder of the alpha alumina powders, and (iii) burnout materials having a particle sizes of 1-10 microns. In some embodiments, an unmilled alpha alumina powder having a particle size of 10 to 100 microns is also included in said precursor mixture. Also described herein is a method for producing a porous body in which the above-described precursor mixture is formed to a given shape, and subjected to a heat treatment step in which the formed shape is sintered to produce the porous body.

14 Claims, No Drawings

OTHER PUBLICATIONS

Green, D. W., Perry's Chemical Engineers' Handbook, 8th Edition, McGraw-Hill, 2007, pp. 58.

Brunauer, S., et al., "Adsorption of Gases in Multimolecular Layers", J. Am. Chem. Soc., Feb. 1938, pp. 309-316, 60.

C. Falamaki, et al., "Dual behavior of CaCO3 as a porosifier and sintering aid in the manufacture of alumina membrane/catalyst supports", Journal of the European Ceramic Society 24, accepted Oct. 25, 2003, pp. 3195-3201.

International Search Report dated Sep. 13, 2016 received in corresponding foreign application.

International Search Report dated Sep. 19, 2016 received in corresponding foreign application.

* cited by examiner

METHOD FOR PRODUCING POROUS BODIES WITH ENHANCED PROPERTIES

CROSS REFERENCE TO RELATED APPLICATIONS

The present invention claims the benefit of U.S. Provisional Patent Application Nos. 62/169,706 and 62/169,766 filed Jun. 2, 2015, the entire content and disclosure of each are incorporated herein by reference.

FIELD OF THE INVENTION

The present invention relates to porous bodies and more particularly to porous bodies that can be used in a wide variety of applications including, for example, as a filter, a membrane, or a catalyst carrier.

BACKGROUND

In the chemical industry and the chemical engineering industry, reliance is oftentimes made on using porous bodies, including porous ceramic bodies that are capable of performing or facilitating separations or reactions and/or providing areas for such separations and reactions to take place. Examples of separations or reactions include: filtration of gases and liquids, adsorption, reverse osmosis, dialysis, ultrafiltration, or heterogeneous catalysis. Although the desired physical and chemical properties of such porous bodies vary depending on the particular application, there are certain properties that are generally desirable in such porous bodies regardless of the final application in which they will be utilized.

For example, porous bodies may be substantially inert so that the porous bodies themselves do not participate in the separations or reactions taking place around, on or through them in a way that is undesired, unintended, or detrimental. In applications where it is desired to have the components that are being reacted or separated pass through, or diffuse into, the porous body, a low diffusion resistance (e.g., high effective diffusivity) would be advantageous.

In some applications, the porous bodies are provided within a reaction or separation space, and so they are desirably of high pore volume and/or high surface area, in order to improve the loading and dispersion of the desired reactants, and also to provide enhanced surface area on which the reactions or separations can take place. These applications also require sufficient mechanical integrity to avoid being damaged, i.e., crushed, chipped or cracked, during transport or placement. However, combination of high mechanical strength with high pore volume in a porous body is not easy to achieve because the strength decreases exponentially with increasing porosity.

In view of the above, there is a need for providing porous bodies that have a pore architecture that has enhanced fluid transport properties, particularly gas diffusion properties and high mechanical integrity. Such pore architectures can be achieved only by the precise control of the porous body precursor mixture and the porous body preparation process, which are described in the present invention.

SUMMARY

In an effort to reduce the level of defects in a porous body, the instant disclosure is directed to methods for producing a porous ceramic body in which such defects can be minimized. In some embodiments, the methods described herein provide porous bodies having appreciable pore volumes, crush strengths, and/or surface areas. In other embodiments, the methods described herein provide porous bodies having a pore architecture that exhibits enhanced fluid transport properties and high mechanical integrity.

The porous bodies of the present invention can be prepared by first providing a precursor mixture, wherein the precursor mixture comprises: (i) milled alpha alumina powder having a particle size of 0.1 to 6 microns, (ii) optionally, unmilled alpha alumina powder having a particle size of 10 to 100 microns (iii) boehmite binder, preferably nanosized, wherein said boehmite functions as a binder of the alpha alumina powders, (iv) burnout material having a particle size of 1-10 microns, and (v) optionally, other additives, such as solvents and lubricants. All components of the porous body precursor mixture are homogeneously mixed.

Another embodiment of the present invention is directed to methods for fabricating a porous body in which the above-described precursor mixture is formed into a shape, and the formed shape is subjected to a heat treatment process to remove volatiles (e.g., water and burnout materials) and sinter the shape into a porous body. In particular embodiments, the fabrication method comprises: (i) dispersing boehmite into water to produce a dispersion of boehmite; (ii) adding a milled alpha alumina powder having a particle size of 0.1 to 6 microns to the dispersion of boehmite, and mixing until a first homogeneous mixture is obtained, wherein said boehmite functions as a binder of the alpha alumina powder; (iii) adding burnout material having a particle size of 1-10 microns, and mixing until a second homogeneous mixture is obtained; (iv) forming the second homogeneous mixture to form a shape of said second homogeneous mixture; (v) subjecting the formed shape to a heat treatment step within a temperature in a range of 35-900° C. to remove water and burn out the burnout material to produce a pre-fired porous body; and (vi) subjecting the pre-fired porous body to a sintering step at a temperature within a range of 900-2000° C. to produce said porous body.

In other aspects, the instant disclosure is also directed to the porous body produced by the above-described method, as well as filters, membranes, catalyst supports, and the like, particularly ethylene oxidation (i.e., epoxidation) catalysts comprising the porous body (i.e., carrier) described above, along with a catalytic amount of silver. In some embodiments, the resulting epoxidation catalyst exhibits an increased catalyst activity and/or a maintained or improved selectivity.

The instant disclosure is also directed to a method for the vapor phase conversion of ethylene to ethylene oxide (EO) by use of the above-described catalyst. The method includes reacting a reaction mixture comprising ethylene and oxygen in the presence of the ethylene epoxidation catalyst described above.

DETAILED DESCRIPTION

In one aspect, the instant disclosure is directed to a method for producing a porous body in which a specially crafted precursor mixture is formed to a shape and subjected to a heat treatment step to produce the porous body. In particular embodiments, the precursor mixture includes at least: (i) milled alpha alumina powder having a particle size of 0.1 to 6 microns, or more typically, 0.25 to 4 microns, (ii) boehmite powder that functions as a binder of the alpha alumina powders, and (iii) burnout material having a particle size of 1-10 microns. In some embodiments, the precursor mixture further includes an unmilled alpha alumina powder having a particle size of 10 to 100 microns, while in other embodiments, the precursor mixture excludes the unmilled alpha alumina. In embodiments, where the unmilled alpha alumina is included, the weight ratio of milled to unmilled alpha alumina powder is generally in a range of 0.25:1 to about 5:1, preferably 0.5 to 4, and more preferably, 0.75 to 3. The term "about" generally indicates no more than ±10%, 5%, or 1% deviation from a value. The precursor mixture may also include one or more additives, such as a solvent and/or lubricant. In some embodiments, the burnout material is selected from at least one of a polyolefin powder and graphite powder, or from both. In embodiments where the burnout material contains both polyolefin and graphite powder, the weight ratio of polyolefin powder to graphite powder is generally in a range of 0.25:1 to about 5:1, preferably in a range of 0.5 to 4, and more preferably 0.75 to 3. Generally, the boehmite is present in an amount of at least 10% or 25% by weight of total alumina content. In some embodiments, a silicon-containing substance is substantially excluded from the precursor mixture.

The method for producing the porous body may also be practiced by adding components in at least two steps prior to the heat treatment step. For example, in some embodiments, a dispersion of boehmite is first produced, i.e., in step (i), by dispersing boehmite particles into water, which may be neutral water or acidified water. As well known in the art, boehmite is an aluminum oxide hydroxide material, generally recognized as conforming with the formula γ-AlO(OH). For purposes of the invention, the boehmite particles, as produced in the dispersion, are preferably nanosized, e.g., up to or less than 200 nm, preferably <100 nm, and more preferably <50 nm. The acid employed in the acidified water is typically a strong mineral acid, such as nitric acid, hydrochloric acid, or sulfuric acid. The acid can be also weak acid, such as, for example, acetic acid. The acid employed in the acidified water can be added to neutral water or be dissolved from solid particles, such as, for example, boehmite.

A milled particulate form of alpha-alumina is then added to the dispersion of boehmite in step (ii), wherein the milled form of alpha-alumina is characterized by an average or median particle size (e.g., $D_{50}$, the particle size where half of the particle population lies below the indicated value) in a range of 0.1 to 6 microns, and preferably 0.25 to 4 microns. The mixture of boehmite and milled alpha-alumina is mixed until a first homogeneous mixture is obtained. The term "homogeneous," as used herein, indicates that individual macroscopic regions of agglomerated particles (i.e., of at least 100 or 200 microns) of each substance in the mixture (e.g., boehmite and alpha-alumina) are typically not detectable or present in the homogeneous mixture, although individual microscopic regions of agglomerated particles (e.g., less than 100 or 200 microns), may or may not be present. In the homogeneous mixture, the boehmite functions as a binder of the alpha alumina particles. In some embodiments, the alpha-alumina has a very high purity, i.e., about 95 or 98 wt % or more. In some embodiments, the alpha-alumina is a low sodium alumina or a low sodium reactive alumina. The term "reactive alumina" as used herein generally indicates an alpha-alumina with good sinterability and having a particle size that is very fine, i.e., generally, of 2 microns or less. Generally, a "low sodium alumina" material contains 0.1% or less sodium content. Good sinterability is generally derived from a 2 micron or less particle size.

The particle sizes given above can refer to a diameter for the case where the particle is spherical or approximately spherical. For cases where the particles substantially deviate from a spherical shape, the particle sizes given above are based on the equivalent diameter of the particles. As known in the art, the term "equivalent diameter" is used to express the size of an irregularly-shaped object by expressing the size of the object in terms of the diameter of a sphere having the same volume as the irregularly-shaped object.

In some embodiments, step (ii) can include, either simultaneous or subsequent to adding and mixing the milled alpha alumina powder, adding unmilled alpha-alumina powder having a $D_{50}$ particle size in a range of about 10-100 microns, and mixing until the first homogeneous mixture is obtained. The term "subsequent" indicates that the additional material (e.g., unmilled alpha-alumina) can be included in the same step (ii) or in a succeeding step before the forming and firing steps (iv) to (vi). Typically, the unmilled alpha-alumina has a $D_{50}$ particle size in a range of 10 to 100 microns, and more preferably 25 to 80 microns.

When unmilled alpha-alumina powder is included, the resulting first homogeneous mixture contains a homogeneous mixture of boehmite, milled alpha-alumina, and unmilled alpha-alumina. In some embodiments, the weight percentage of milled alpha-alumina is greater than the weight percentage of unmilled alpha-alumina, by weight of total alumina. For example, the milled and unmilled alpha aluminas can be present in a weight ratio (i.e., milled to unmilled alumina) of about, at least, or above 1.1:1, 1.5:1, 1.8:1, or 2:1 and to up to or less than 1.5:1, 1.8:1, 2:1, or 2.5:1. In other embodiments, the weight percentage of unmilled alpha-alumina is greater than the weight percentage of milled alpha-alumina, by weight of total alumina. For example, the unmilled and milled alpha aluminas can be present in a weight ratio (i.e., unmilled to milled alumina) of at least or above 1.1:1 or 1.5:1 and to up to or less than 1.8:1, 2:1, or 2.5:1. In other embodiments, the weight ratio of milled to unmilled alpha-alumina is about or at least 0.25:1 or 0.5:1 and/or about, up to, or less than 2.5:1 or 3:1. In some embodiments, the milled alpha alumina is the only alumina used in step (ii) or the only alumina employed in the method and incorporated into the porous body, i.e., unmilled alpha alumina is excluded from the method. In other embodiments, the combination of milled and unmilled alpha aluminas is the only alumina used in step (ii) or the only alumina employed in the method and incorporated into the porous body.

In some embodiments, the weight percentage of boehmite is about the same or less than the weight percentage of total alumina. For example, the boehmite may be present in an amount of at least or above 5% or 10%. In some embodiments, the weight percentage of boehmite is about the same or greater than the weight percentage of total alumina. For example, the boehmite may be present in an amount of at least or above 25% by weight of total alumina content. The total alumina used in the method in the porous body precursor is typically at least or above 25% or 35% by weight of total weight of solid components incorporated into the porous body.

After formation of the first homogeneous mixture containing boehmite and alpha-alumina in step (ii), a burnout material having a particle size of 1-10 microns is added to and mixed into the first homogeneous mixture until a second homogeneous mixture is obtained, i.e., in step (iii). The second homogeneous mixture preferably consists of free-flowing particles that can be subsequently formed to a shape and sintered. The burnout material, which may also be considered a temporary binder, can be any of the burnout materials known in the art, such as granulated polyolefins (e.g., polyethylene or polypropylene), graphite, cellulose, substituted celluloses (e.g., methylcellulose, ethylcellulose, and carboxyethylcellulose), stearates (such as organic stearate esters, e.g., methyl or ethyl stearate), waxes, walnut shell flour, and the like, which are decomposable at the temperatures employed. The burnout material is primarily responsible for imparting porosity to the porous body, and to ensure the preservation of a porous structure during the green (i.e., unfired phase) in which the mixture may be shaped into particles by molding or extrusion processes. Burnout materials are generally substantially or completely removed during firing to produce the finished porous body. In different embodiments, the burnout material may have a particle size in a range of about, for example, 1-10 microns, preferably 1-9 microns, and more preferably 1.5-8 microns.

In particular embodiments, the burnout material used in step (iii) is a granulated polyolefin (e.g., polyethylene), or graphite powder, or both. If both the polyolefin and graphite are used, they can have the same or different particle sizes, and they can be added simultaneously or sequentially. For example, in some embodiments, after a granulated polyolefin is added and mixed until a second homogeneous mixture is obtained, graphite may be added subsequently, wherein the term "subsequently" or "sequentially" indicates that the additional material can be included in the same step (iii) or in a succeeding step before the forming and firing steps (iv) to (vi). In some embodiments, the granulated polyolefin is included in an amount by weight greater than the amount by weight of graphite. For example, the weight ratio of granulated polyolefin to graphite may be 0.25:1 to about 5:1, and preferably 0.75 to about 3.5. In other embodiments, the granulated polyolefin is included in an amount by weight less than the amount by weight of graphite. For example, the weight ratio of graphite to granulated polyolefin may be 0.25:1 to about 5:1, and preferably 1 to about 2.5.

In one embodiment, steps (i), (ii), and (iii) are separated and conducted in succession, i.e., the dispersion of boehmite is produced in step (i), followed by production of the first homogeneous mixture in step (ii), followed by production of the second homogenous mixture in step (iii). Steps (i), (ii), and (iii) can be also conducted in reverse or in random order. In another embodiment, steps (i) and (ii) may be combined as a single step, i.e., boehmite and alumina are combined in the presence of acidified water to form a dispersion of boehmite and alumina, which functions as the first homogeneous mixture. In yet another embodiment, steps (ii) and (iii) may be combined as a single step, i.e., alumina and burnout material are combined during production of the first homogeneous mixture, which now also functions as the second homogeneous mixture. In a further embodiment, steps (i), (ii), and (iii) may be combined as a single step, i.e., boehmite, alumina, and burnout material are combined in the presence of acidified water to form a dispersion of boehmite, alumina, and burnout material, which functions as the second homogeneous mixture.

In some embodiments, the method further includes (in any step prior to forming and firing the second homogeneous mixture) a binder material in sufficient amount. Permanent binders include, for example, inorganic clay-type materials, such as silica and an alkali or alkali earth metal compound. A convenient binder material which may be incorporated with the alumina particles comprises boehmite, a stabilized silica sol, and optionally alkali or alkali earth metal salt. In some embodiments, a silicon-containing substance is substantially or completely excluded from the method for producing the porous body. In the case of a silicon-containing substance being substantially excluded from the porous body, a trace amount of silicon derived from impurities in the raw materials used to prepare the porous body may still be present in the porous body. Such trace amounts are generally no more than 1%, 0.5%, or 0.1% by weight of the porous body.

The precursor mixture, or the second homogeneous mixture formed in step (iii), is then formed into a desired shape by means well known in the art. The forming process can be by extrusion, pressing, pelletizing, molding, casting, etc. After forming, the formed shape is subjected to a heat treatment step in which it is sintered to produce the porous body. The sintering process generally employs a temperature in a range of about 900° C. to about 2000° C. The sintering step would also necessarily function to remove volatiles, such as water and the burnout material. However, in some embodiments, a preceding lower temperature heat treatment (also referred to herein as a "pre-firing step") is conducted before the sintering step in order to remove such volatiles. The preceding lower temperature heat treatment generally employs a temperature of about 35° C. to about 900° C. Generally, a heating and/or cooling rate within a range of 0.5-100° C./min, preferably 1-20° C./min, or more preferably 2-5° C./min, is used.

In order to properly characterize porous bodies for applications in filters, membranes, or catalyst carriers, pore architecture and consequently fluid transport-related properties must also be determined.

Among very important parameters in determining the diffusive gas transport through a porous body are tortuosity and constriction. Tortuosity is determined by the ratio of the real length of flow path through a porous body to the shortest distance across that porous body (see, for example, B. Ghanbarian et al., *Soil Sci. Soc. Am. J.*, 77, 1461-1477 (2013)). Constriction is a function of the area ratio of large pores to small pores. Thus, lowering the values of tortuosity and/or constriction enhances the diffusive transport through a porous material, i.e., increases the effective diffusivity, which is very important for instance in catalytic applications.

If there is a pressure drop across the porous body, permeability becomes important. Permeability indicates ability of fluids to flow through porous bodies and can be described by the Darcy's law shown in Equation 1, where V is fluid flow velocity, k is permeability, $\mu$ is dynamic viscosity of the fluid, $\Delta P$ is pressure difference across porous body with thickness of $\Delta x$:

$$V = \frac{k}{\mu} \frac{\Delta P}{\Delta x} \qquad (\text{Eq. 1})$$

Thus higher values of permeability will enhance the pressure-driven fluid flow across a porous body, which is important in such applications as sorption, filtration, or catalysis.

Surprisingly, the aforementioned fluid transport-determining properties of porous bodies cannot be found in the literature to characterize porous architectures, particularly as related to catalyst carriers for epoxidation of olefins. Moreover, there has been no indication in the literature of the necessary values of tortuosity, constriction or permeability which provide a pore architecture to a porous body that can achieve enhanced properties, especially in regard to catalyst performance. The present invention provides porous bodies that have a pore architecture that has enhanced fluid transport properties and high mechanical integrity.

Unless otherwise specified the following methodology of measurements were employed in the present application:

In the present invention, water absorption of the porous bodies was measured by placing a 10 g representative sample of a porous body into a flask, which was then evacuated to about 0.1 torr for 5 min. Subsequently, deionized water was aspirated into the evacuated flask to cover the porous bodies while maintaining the pressure at about 0.1 torr. The vacuum was released after about 5 minutes to restore ambient pressure, hastening complete penetration of water into the pores. Subsequently, the excess water was drained from the impregnated sample. Water absorption was calculated by dividing total water weight in the pores (i.e., wet mass-dry mass of the sample) by the weight of the dry sample at room temperature.

Cumulative intrusion curves and Log differential intrusion curves may be acquired for representative samples of the porous bodies by mercury (Hg) intrusion porosimetry, principles of which are described in Lowell et al., *Characterization of Porous Solids and Powders: Surface Area, Pore Size and Density*, Springer, 2006. The Hg intrusion pressure may range between, for example, 1.5 and 60,000 psi, which corresponds to pore sizes between 140 microns and 3.6 nm. The following Hg parameters may be used for calculations: surface tension of 480 dynes/cm, density of 13.53 g/mL, and contact angle of 140°. Pore volumes for the porous bodies may be measured from the Hg intrusion data, which are consistent with the water absorption measurements. Additional pore architecture parameters of the porous bodies, such as tortuosity, constriction, and permeability, may also be calculated from the Hg intrusion data, as discussed below.

The tortuosity, $\xi$, was calculated from Equation 2, where $D_{avg}$ is weighted average pore size, k is permeability, $\rho$ is true materials density, and $I_{tot}$ is total specific intrusion volume (see, for example, *AutoPore V Operator Manual*, Micromeritics, 2014):

$$\xi = \sqrt{\frac{D_{avg}^2}{4 \cdot 24k(1-\rho I_{tot})}} \quad \text{(Eq. 2)}$$

The constriction, $\sigma$, was calculated from Equation 3, where $\xi$ is tortuosity and $\tau$ is tortuosity factor, calculated from the Carnigilia equation (see, for example, *AutoPore V Operator Manual*, Micromeritics, 2014):

$$\sigma = \frac{\xi}{\tau} \quad \text{(Eq. 3)}$$

The permeability, as defined by the Darcy's law (Eq. 1, above) can be calculated by combining Darcy's and Poiseuille'd equations (see, for example, Lowell et al., *Characterization of Porous Solids and Powders*, Springer, 2006). For an arbitrary pore shape factor, f, the permeability k is expressed by Equation 4, where $\tau$ is tortuosity factor, P is materials porosity, and d is pore diameter:

$$k = \frac{P^3 d^2}{16 f \tau (1-P)^2} \quad \text{(Eq. 4)}$$

Once tortuosity and pore volumes have been measured, effective diffusivity can be calculated from Equation 5, where P is materials porosity, D is diffusivity, $D_{eff}$ is effective diffusivity, and $\xi$ is tortuosity [D. W. Green, R. H. Perry, *Perry's Engineering Handbook*, $8^{th}$ Edition, McGraw-Hill, 2007]

$$D_{eff} = \frac{PD}{\xi} \quad \text{(Eq. 5)}$$

In order to calculate absolute values of effective diffusivity, $D_{eff}$, in a porous solid, absolute values of gas diffusivity, D, must be known per Eq. 5, in addition to the material porosity and tortuosity. However, in order to compare effective diffusivity properties of different porous solids (e.g., inventive examples of the present invention), it is possible to calculate relative numbers of effective diffusivity normalized to a standard material (comparative example of the present invention). With the assumption that gas diffusivity, D, is the same in all cases, it requires only knowledge of porosity and tortuosity of the porous materials (see Equation 6).

$$\frac{D_{eff,1}}{D_{eff,0}} = \frac{P_1}{\xi_1} \frac{\xi_0}{P_0} \quad \text{(Eq. 6)}$$

Total porosity is defined as the void volume divided by the total volume of the sample. It can be calculated from mercury porosimetry or water absorption, using theoretical density of the carrier material.

The porous body of the present invention typically has a pore volume from 0.3 mL/g to 1.2 mL/g. More typically, the porous body of the present invention has a pore volume from 0.35 mL/g to 0.9 mL/g. In some embodiments of the present invention, the porous body of the present invention has a water absorption from 30 percent to 120 percent, with a range from 35 percent to 90 percent being more typical.

The porous body of the present invention typically has a B.E.T. surface area from 0.3 $m^2$/g to 3.0 $m^2$/g. In one embodiment, the porous body of the present invention has a surface area from 0.5 $m^2$/g to 1.2 $m^2$/g. In another embodiment body of the present invention has a surface area above 1.2 $m^2$/g up to, and including, 3.0 $m^2$/g. The B.E.T. surface area described herein can be measured by any suitable method, but is more preferably obtained by the method described in Brunauer, S., et al., *J. Am. Chem. Soc.*, 60, 309-16 (1938).

The porous body of the present invention can be monomodal, or multimodal, such as, for example, bimodal. The porous body of the present invention has a pore size distribution with at least one mode of pores in the range from 0.01 micrometers to 100 micrometers. In one embodiment of the present invention, at least 90 percent of the pore volume of the porous body is attributed to pores having a pore size of 20 microns or less. In yet another embodiment of the present invention, at least 85 percent of the pore volume of the porous body is attributed to pores having a size from 1 micron to 6 microns. In yet a further embodiment of the present invention, less than 15, preferably less than 10, percent of the pore volume of the porous body is attributed to pores having a size of less than 1 micron. In still a further embodiment of the present application at least 80 percent of the pore volume of the porous body is attributed to pores having a size from 1 micron to 10 microns. In a particular aspect of the present invention, there are essentially no pores smaller than 1 micron.

In the case of a multimodal pore size distribution, each pore size distribution can be characterized by a single mean pore size (mean pore diameter) value. Accordingly, a mean pore size value given for a pore size distribution necessarily corresponds to a range of pore sizes that results in the indicated mean pore size value. Any of the exemplary pore sizes given above can alternatively be understood to indicate a mean (i.e., average or weighted average) pore size. Each peak pore size can be considered to be within its own pore size distribution (mode), i.e., where the pore size concentration on each side of the distribution falls to approximately zero (in actuality or theoretically). The multimodal pore size distribution can be, for example, bimodal, trimodal, or of a higher modality. In one embodiment, different pore size distributions, each having a peak pore size, are non-overlapping by being separated by a concentration of pores of approximately zero (i.e., at baseline). In another embodiment, different pore size distributions, each having a peak pore size, are overlapping by not being separated by a concentration of pores of approximately zero.

In one embodiment, the porous body of the present invention may be bimodal having a first set of pores from 0.01 microns to 1 micron and a second set of pores from greater than 1 micron to 10 microns. In such an embodiment, the first set of pores may constitute less that 15 percent of the total pore volume of the porous body, while the second set of pores may constitute more than 85 percent of the total pore volume of the porous body. In yet another embodiment, the first set of pores may constitute less than 10 percent of the total pore volume of the porous body, while the second set of pores may constitute more than 90 percent of the total pore volume of the porous body.

The porous body of the present invention typically has a total porosity that is from 55 percent to 83 percent. More typically, the porous body of the present invention typically has a total porosity that is from 58 percent to 78 percent.

The porous body of the present invention typically has an average flat plate crush strength from 10 N to 150 N. More typically, the porous body of the present invention typically has an average flat plate crush strength from 40 N to 105 N. The flat plate crush strength of the porous bodies was measured using a standard test method for single pellet crush strength of formed catalysts and catalyst carriers, ASTM Standard ASTM D4179.

In some embodiments, the porous body of the present invention can have an attrition value that is less than 40%, preferably less than 25%. In some embodiments of the present invention, the porous body can have attrition less that 10%. Attrition measurements of the porous bodies were performed using a standard test method for attrition and abrasion of catalysts and catalyst carriers, ASTM Standard ASTM D4058.

In some embodiments of the present invention, the porous body of the present invention has an initial low alkali metal content. By "low alkali metal content" it is meant that the porous body contains from 2000 ppm or less, typically from 30 ppm to 300 ppm, of alkali metal therein. Porous bodies containing low alkali metal content can be obtained by adding substantially no alkali metal during the porous body manufacturing process. By "substantially no alkali metal" it is meant that only trace amounts of alkali metal are used during the porous body manufacture process as impurities from other constituents of the porous body. In another embodiment, a porous body having a low alkali metal content can be obtained by performing various washing steps to the porous body precursor materials used in forming the porous body. The washing steps can include washing in a base, water, or an acid.

In other embodiments of the present invention, the porous body has an alkali metal content that is above the value mentioned above for the porous body having substantially no alkali metal content. In such an embodiment the porous body typically contains a measurable level of sodium on the surface thereof. The concentration of sodium at the surface of the carrier will vary depending on the level of sodium within the different components of the porous body as well as the details of its calcination. In one embodiment of the present invention, the porous body has a surface sodium content of from 2 ppm to 150 ppm, relative to the total mass of the porous body. In another embodiment of the present invention, the porous body has a surface sodium content of from 5 ppm to 70 ppm, relative to the total mass of the carrier. The sodium content mentioned above represents that which is found at the surface of the carrier and that which can be leached, i.e., removed, by, for example, nitric acid (hereafter referred to as acid-leachable sodium).

The quantity of acid leachable sodium present in the porous bodies of the present invention can be extracted from the catalyst or carrier with 10% nitric acid in deionized water at 100° C. The extraction method involves extracting a 10-gram sample of the catalyst or carrier by boiling it with a 100 ml portion of 10% w nitric acid for 30 minutes (1 atm., i.e., 101.3 kPa) and determining in the combined extracts the relevant metals by using a known method, for example atomic absorption spectroscopy (See, for example, U.S. Pat. No. 5,801,259 and U.S. Patent Application Publication No. 2014/0100379 A1).

In one embodiment of the present invention, the porous body may have a silica content, as measured as $SiO_2$, of less than 0.2, preferably less than 0.1, weight percent, and a sodium content, as measured as $Na_2O$, of less than 0.2 weight percent, preferably less than 0.1 weight percent. In some embodiments, the porous body of the present invention may have an acid leachable sodium content of 40 ppm or less. In yet further embodiments of the present invention, the porous body comprises alumina crystallites having a platelet morphology in a content of less than 20 percent by volume. In some embodiments, the alumina crystallites having a platelet morphology in a content of less than 10 percent by volume are present in the porous body of the present invention.

In addition to the above physical properties, the porous body of the present invention has a pore architecture that provides at least one of a tortuosity of 7 or less, a constriction of 4 or less and a permeability of 30 mdarcys or greater. A porous body that has the aforementioned pore architecture has enhanced fluid transport properties and high mechanical integrity. In some embodiments, and when used as a carrier for a silver-based epoxidation catalyst, a porous body having the aforementioned pore architecture can exhibit improved catalyst properties. Typically, the pore architecture of the porous body of the present invention has a tortuosity of 7 or less and/or a constriction of 4 or less.

In one embodiment of the present invention, the porous body has a pore architecture that provides a tortuosity of 7 or less. In another embodiment, the porous body of the present invention has a pore architecture that provides a tortuosity of 6 or less. In yet another embodiment, the porous body of the present invention has a pore architecture that provides a tortuosity of 5 or less. In a further embodiment, the porous body of the present invention has a pore architecture that provides a tortuosity of 3 or less. The lower limit of the tortuosity of the porous body of the present invention is 1 (theoretical limit). In some embodiments, the tortuosity can be any number bounded between 1 and 7.

In one embodiment of the present invention, the porous body has a pore architecture that provides a constriction of 4 or less. In another embodiment, the porous body of the present invention has a pore architecture that provides a constriction of 3 or less, or even 2 or less. The lower limit of the constriction of the porous body of the present invention is 1. In some embodiments, the constriction can be any number bounded between 1 and 4.

In another embodiment of the present invention, the porous body has 2-4 times improved effective gas diffusivity due to the combination of low tortuosity and high porosity.

In one embodiment, the porous body of the present invention has a pore architecture that provides a permeability of 30 mdarcys or greater. In another embodiment, the porous body of the present invention has a pore architecture that provides a permeability of 200 mdarcys or greater.

The porous body can be of any suitable shape or morphology. For example, the carrier can be in the form of particles, chunks, pellets, rings, spheres, three-holes, wagon wheels, cross-partitioned hollow cylinders, and the like, of a size preferably suitable for employment in fixed bed reactors.

In one embodiment, the porous body contains essentially only alumina, or alumina and boehmite components, in the absence of other metals or chemical compounds, except that trace quantities of other metals or compounds may be present. A trace amount is an amount low enough that the trace species does not observably affect functioning or ability of the catalyst.

In another embodiment, the porous body may be used as a catalyst carrier (i.e., catalyst support), in which case it typically contains one or more catalytically active species, typically metals, disposed on or in the porous body. The one or more catalytically active materials can catalyze a specific reaction and are well known in the art. In some embodiments, the catalytically active material includes one or more transition metals from Groups 3-14 of the Periodic Table of Elements and/or lanthanides. In such applications, one or more promoting species (i.e., species that aide in a specific reaction) can be also disposed on or in the porous body of the present invention. The one or more promoting species may be, for example, alkali metals, alkaline earth metals, transition metals, and/or an element from Groups 15-17 of the Periodic Table of Elements.

In the particular case of the porous body being used as a carrier for silver-based epoxidation catalysis, the carrier includes silver on and/or in the porous body. Thus, in the method described above, generally after the sintering step, the silver is incorporating on or into the carrier by means well known in the art, e.g., by impregnation of a silver salt followed by thermal treatment, as well known in the art, as described in, for example, U.S. Pat. Nos. 4,761,394, 4,766,105, 4,908,343, 5,057,481, 5,187,140, 5,102,848, 5,011,807, 5,099,041 and 5,407,888, all of which are incorporated herein by reference. The concentration of silver salt in the solution is typically in the range from about 0.1% by weight to the maximum permitted by the solubility of the particular silver salt in the solubilizing agent employed. More typically, the concentration of silver salt is from about 0.5% by weight of silver to 45% by weight of silver, and even more typically, from about 5% by weight of silver to 35% by weight of silver by weight of the carrier. The foregoing amounts are typically also the amounts by weight found in the catalyst after thermal treatment. To be suitable as an ethylene epoxidation catalyst, the amount of silver should be a catalytically effective amount for ethylene epoxidation, which may be any of the amounts provided above.

In addition to silver, the silver-based epoxidation catalyst of the present invention may also include any one or more promoting species in a promoting amount. The one or more promoting species can be incorporated into the porous body described above either prior to, coincidentally with, or subsequent to the deposition of the silver. As used herein, a "promoting amount" of a certain component of a catalyst refers to an amount of that component that works effectively to provide an improvement in one or more of the catalytic properties of the catalyst when compared to a catalyst not containing said component.

For example, the silver-based epoxidation catalyst may include a promoting amount of a Group I alkali metal or a mixture of two or more Group 1 alkali metals. Suitable Group 1 alkali metal promoters include, for example, lithium, sodium, potassium, rubidium, cesium or combinations thereof. Cesium is often preferred, with combinations of cesium with other alkali metals also being preferred. The amount of alkali metal will typically range from about 10 ppm to about 3000 ppm, more typically from about 15 ppm to about 2000 ppm, more typically from about 20 ppm to about 1500 ppm, and even more typically from about 50 ppm to about 1000 ppm by weight of the total catalyst, expressed in terms of the alkali metal.

The silver-based epoxidation catalyst may also include a promoting amount of a Group 2 alkaline earth metal or a mixture of two or more Group 2 alkaline earth metals. Suitable alkaline earth metal promoters include, for example, beryllium, magnesium, calcium, strontium, and barium or combinations thereof. The amounts of alkaline earth metal promoters are used in similar amounts as the alkali metal promoters described above.

The silver-based epoxidation catalyst may also include a promoting amount of a main group element or a mixture of two or more main group elements. Suitable main group elements include any of the elements in Groups 13 (boron group) to 17 (halogen group) of the Periodic Table of the Elements. In one example, a promoting amount of one or more sulfur compounds, one or more phosphorus compounds, one or more boron compounds or combinations thereof can be used.

The silver-based epoxidation catalyst may also include a promoting amount of a transition metal or a mixture of two or more transition metals. Suitable transition metals can include, for example, the elements from Groups 3 (scandium group), 4 (titanium group), 5 (vanadium group), 6 (chromium group), 7 (manganese group), 8-10 (iron, cobalt, nickel groups), and 11 (copper group) of the Periodic Table of the Elements, as well as combinations thereof. More typically, the transition metal is an early transition metal selected from Groups 3, 4, 5, 6, or 7 of the Periodic Table of Elements, such as, for example, hafnium, yttrium, molybdenum, tungsten, rhenium, chromium, titanium, zirconium, vanadium, tantalum, niobium, or a combination thereof.

In one embodiment of the present invention, the silver-based epoxidation catalyst includes silver, cesium, and rhenium. In another embodiment of the present invention, the silver-based epoxidation catalyst includes silver, cesium, rhenium and one or more species selected from Li, K, W, Zn, Mo, Mn, and S.

The silver-based epoxidation catalyst may also include a promoting amount of a rare earth metal or a mixture of two or more rare earth metals. The rare earth metals include any of the elements having an atomic number of 57-71, yttrium (Y) and scandium (Sc). Some examples of these elements include lanthanum (La), cerium (Ce), and samarium (Sm).

The transition metal or rare earth metal promoters are typically present in an amount of from about 0.1 micromoles per gram to about 10 micromoles per gram, more typically from about 0.2 micromoles per gram to about 5 micromoles per gram, and even more typically from about 0.5 micromoles per gram to about 4 micromoles per gram of total catalyst, expressed in terms of the metal. All of the aforementioned promoters, aside from the alkali metals, can be in any suitable form, including, for example, as zerovalent metals or higher valent metal ions.

The silver-based epoxidation catalyst may also include an amount of rhenium (Re), which is known as a particularly efficacious promoter for ethylene epoxidation high selectivity catalysts. The rhenium component in the catalyst can be in any suitable form, but is more typically one or more rhenium-containing compounds (e.g., a rhenium oxide) or complexes. The rhenium can be present in an amount of, for example, about 0.001 wt. % to about 1 wt. %. More typically, the rhenium is present in amounts of, for example, about 0.005 wt. % to about 0.5 wt. %, and even more typically, from about 0.01 wt. % to about 0.05 wt. % based on the weight of the total catalyst including the support, expressed as rhenium metal. All of these promoters, aside from the alkali metals, can be in any suitable form, including, for example, as zerovalent metals or higher valent metal ions.

After impregnation with silver and any promoters, the impregnated carrier is removed from the solution and calcined for a time sufficient to reduce the silver component to metallic silver and to remove volatile decomposition products from the silver-containing support. The calcination is typically accomplished by heating the impregnated carrier, preferably at a gradual rate, to a temperature in a range of about 200° C. to about 600° C., more typically from about 200° C. to about 500° C., more typically from about 250° C. to about 500° C., and more typically from about 200° C. or 300° C. to about 450° C., at a reaction pressure in a range from about 0.5 to about 35 bar. In general, the higher the temperature, the shorter the required calcination period. A wide range of heating periods have been described in the art for the thermal treatment of impregnated supports. See, for example, U.S. Pat. No. 3,563,914, which indicates heating for less than 300 seconds, and U.S. Pat. No. 3,702,259, which discloses heating from 2 to 8 hours at a temperature of from 100° C. to 375° C. to reduce the silver salt in the catalyst. A continuous or step-wise heating program may be used for this purpose. During calcination, the impregnated support is typically exposed to a gas atmosphere comprising an inert gas, such as nitrogen. The inert gas may also include a reducing agent.

In another embodiment, the porous body described above can also be used as a filter in which liquid or gas molecules can diffuse through the pores of the porous body described above. In such an application, the porous body can be placed along any portion of a liquid or gas stream flow. In yet another embodiment of the present invention, the porous body described above can be used as a membrane.

In another aspect, the invention is directed to a method for the vapor phase production of ethylene oxide by conversion of ethylene to ethylene oxide in the presence of oxygen by use of the silver-based epoxidation catalyst described above. Generally, the ethylene oxide production process is conducted by continuously contacting an oxygen-containing gas with ethylene in the presence of the catalyst at a temperature in the range from about 180° C. to about 330° C., more typically from about 200° C. to about 325° C., and more typically from about 225° C. to about 270° C., at a pressure which may vary from about atmospheric pressure to about 30 atmospheres depending on the mass velocity and productivity desired. Pressures in the range of from about atmospheric to about 500 psi are generally employed. Higher pressures may, however, be employed within the scope of the invention. Residence times in large-scale reactors are generally on the order of about 0.1 to about 5 seconds. A typical process for the oxidation of ethylene to ethylene oxide comprises the vapor phase oxidation of ethylene with molecular oxygen in the presence of the inventive catalyst in a fixed bed, tubular reactor. Conventional commercial fixed bed ethylene oxide reactors are typically in the form of a plurality of parallel elongated tubes (in a suitable shell). In one embodiment, the tubes are approximately 0.7 to 2.7 inches O.D. and 0.5 to 2.5 inches I.D. and 15-45 feet long filled with catalyst.

In some embodiments, the silver-based epoxidation catalyst described above exhibits a high level of selectivity in the oxidation of ethylene with molecular oxygen to ethylene oxide. For example, a selectivity value of at least about 83 mol % up to about 93 mol % may be achieved. In some embodiments, the selectivity is from about 87 mol % to about 93 mole %. The conditions for carrying out such an oxidation reaction in the presence of the silver-based epoxidation catalyst described above broadly comprise those described in the prior art. This applies, for example, to suitable temperatures, pressures, residence times, diluent materials (e.g., nitrogen, carbon dioxide, steam, argon, and methane), the presence or absence of moderating agents to control the catalytic action (e.g., 1,2-dichloroethane, vinyl chloride or ethyl chloride), the desirability of employing recycle operations or applying successive conversion in different reactors to increase the yields of ethylene oxide, and any other special conditions which may be selected in processes for preparing ethylene oxide.

In the production of ethylene oxide, reactant feed mixtures typically contain from about 0.5 to about 45% ethylene and from about 3 to about 15% oxygen, with the balance comprising comparatively inert materials including such substances as nitrogen, carbon dioxide, methane, ethane, argon and the like. Only a portion of the ethylene is typically reacted per pass over the catalyst. After separation of the desired ethylene oxide product and removal of an appropriate purge stream and carbon dioxide to prevent uncontrolled build up of inert products and/or by-products, unreacted materials are typically returned to the oxidation reactor.

Examples have been set forth below for the purpose of further illustrating the invention. The scope of this invention is not to be in any way limited by the examples set forth herein.

Examples

Preparation and Characterization of Alumina-Based Porous Supports

Typical compositions of the precursor mixtures of the porous bodies of the present invention are shown in Table 1. Porous bodies of the present invention were typically prepared under constant stirring by (i) dispersing boehmite in water; (ii) adding milled and/or unmilled alpha alumina powder; (iii) adding burn-out 1, if any; (iv) adding burn-out 2 if any; and (v) adding lubricant. Particular quantities and types of the individual constituents of each precursor mixture of the present invention are shown in Table 1. Subsequently, the mixture was extruded using 2" Bonnot extruder with a single die to produce extrudate in the shape of hollow cylinders. The extrudates were cut into equal-length pieces and then dried under a heat lamp for 1 hr. Subsequently, the cut and dried extrudates were moved to a furnace and subjected to the following heat treatments: (i) pyrolysis of the burn-out was performed in flowing air at 800° C. for 16 hrs with average heating rate of 23° C./hr; followed by (ii) sintering at 1250-1550° C. for 12 hrs with a heating and cooling rates of 2.0° C./min.

The following compositions were produced and analyzed, and the results provided in the following tables:

TABLE 1

Ranges of compositions of porous body precursors

| Precursor for Porous Body No. | Unmilled Alpha Alumina Powder (g) | Milled Alpha Alumina Powder (g) | Boehmite (g) | Solvents and Lubricants Total (g) | Burn-out 1 (g) | Burn-out 2 (g) |
|---|---|---|---|---|---|---|
| PB1 (Inventive Example) | 250-500 | 500-700 | 100-300 | 500-700 | 250-500 | 0-200 |
| PB2 (Inventive Example) | 0-250 | 500-700 | 200-400 | 500-800 | 300-600 | 150-350 |
| PB3 (Inventive Example) | 200-450 | 500-700 | 150-350 | 600-950 | 350-650 | 100-300 |
| PB4 (Inventive Example) | 600-900 | 500-700 | 100-250 | 500-700 | 250-450 | — |
| PB5 (Inventive Example) | 500-700 | 700-900 | 100-250 | 500-700 | 250-450 | — |
| PB6 (Inventive Example) | 1,500 | — | 100-250 | 700-900 | — | — |
| PB7 (Inventive Example) | 0-150 | 500-700 | 150-350 | 500-700 | 350-550 | 100-300 |
| PB8 (Comparative Example) | Comparative Example PB8 was made using a different methodology, not of the present invention | | | | | |

TABLE 2

Ranges of properties for different porous bodies

| Porous Body Composition No. | Pore Volume (mL/g) | BET Surface Area (m²/g) | Average Crush Strength (N) | Tortuosity (—) | Constriction (—) | Permeability (mdarcy) | Effective Diffusivity normalized to PB8 |
|---|---|---|---|---|---|---|---|
| PB1 (Inventive Example) | 0.55-0.62 | 0.9-1.0 | 51-77 | 3.8 | 2.6 | 220 | 2.38 |
| PB2 (Inventive Example) | 0.66-0.84 | 0.6-1.2 | 37-60 | 3.3 | 2.3 | 88 | 2.88 |
| PB3 (Inventive Example) | 0.58-0.82 | 0.7-0.9 | 10-62 | 3.1 | 2.2 | 241 | 3.04 |
| PB4 (Inventive Example) | 0.49-0.53 | 0.9-1.2 | 46-60 | 2.4 | 1.6 | 397 | 3.60 |
| PB5 (Inventive Example) | 0.43-0.52 | 0.6-1.1 | 51-105 | 2.5 | 1.7 | 678 | 3.49 |
| PB6 (Inventive Example) | 0.35-0.45 | 0.7-0.8 | 43-74 | 3.1 | 2.1 | 731 | 2.74 |
| PB7 (Inventive Example) | 0.60-0.90 | 1.0-2.2 | 64-94 | 4.3 | 3.0 | 37 | 2.21 |
| PB8 (Comparative Example) | 0.35-0.55 | 0.4-1.0 | 50-80 | 8.3 | 5.3 | 15 | 1.00 |

While there have been shown and described what are presently believed to be the preferred embodiments of the present invention, those skilled in the art will realize that other and further embodiments can be made without departing from the spirit and scope of the invention described in this application, and this application includes all such modifications that are within the intended scope of the claims set forth herein.

What is claimed is:

1. A precursor mixture for producing a porous body, wherein the precursor mixture comprises: (i) at least one milled alpha alumina powder having a particle size of 0.1 to 6 microns, (ii) boehmite powder that functions as a binder of the alpha alumina powders, and (iii) at least one burnout material having a particle size of 1-10 microns.

2. The precursor mixture of claim 1, further comprising unmilled alpha alumina powder having a particle size of 10 to 100 microns.

3. The precursor mixture of claim 2, wherein the weight ratio of milled to unmilled alpha alumina powder is in a range of 0.25:1 to about 5:1.

4. The precursor mixture of claim 1, wherein unmilled alpha alumina powder is excluded from the precursor mixture.

5. The precursor mixture of claim 1, further comprising an additive selected from solvents and lubricants.

6. The precursor mixture of claim 1, wherein said burnout material is selected from at least one of a polyolefin powder and graphite powder.

7. The precursor mixture of claim 1, wherein said burnout material is selected from both a polyolefin powder and graphite powder.

8. The precursor mixture of claim 7, wherein the weight ratio of polyolefin powder to graphite powder is in a range of 0.25:1 to about 5:1.

9. The precursor mixture of claim 1, wherein the boehmite is present in an amount of at least 10% by weight of total alumina content.

10. The precursor mixture of claim 1, wherein the boehmite is present in an amount of at least 25% by weight of total alumina content.

11. The precursor mixture of claim 1, wherein the boehmite is nano-sized powder with dispersed particle size <100 nm.

12. The precursor mixture of claim 1, wherein said milled alpha alumina powder has a particle/crystallite size of 0.25-4 microns.

13. The precursor mixture of claim 1, wherein a silicon-containing substance is substantially excluded from the precursor mixture.

14. The precursor mixture of claim 1, wherein a sodium-containing substance is substantially excluded from the precursor mixture.

* * * * *